United States Patent [19]
Parra

[11] Patent Number: 6,144,175
[45] Date of Patent: Nov. 7, 2000

[54] LOW-VOLTAGE BALLAST-FREE ENERGY-EFFICIENT ULTRAVIOLET MATERIAL TREATMENT AND PURIFICATION SYSTEM AND METHOD

[76] Inventor: Jorge M. Parra, 8210 Sycamore Dr., New Port Richey, Fla. 34654

[21] Appl. No.: 09/168,850

[22] Filed: Oct. 9, 1998

Related U.S. Application Data

[63] Continuation-in-part of application No. 08/964,824, Nov. 5, 1997, Pat. No. 6,034,485.

[51] Int. Cl.[7] .................................................. G05F 1/00
[52] U.S. Cl. ....................... 315/307; 315/219; 315/209 R
[58] Field of Search .............................. 315/206, 219, 315/223, 224, 237, 276, 209 R, 307, DIG. 4, DIG. 7

[56] References Cited

U.S. PATENT DOCUMENTS

| | | | |
|---|---|---|---|
| 4,172,981 | 10/1979 | Smith ............................................ | 307/66 |
| 4,482,809 | 11/1984 | Maarschalkerweerd ................. | 250/436 |
| 4,872,980 | 10/1989 | Maarschalkerweerd ................. | 250/243 |
| 5,023,518 | 6/1991 | Mans et al. ............................... | 315/219 |
| 5,081,399 | 1/1992 | Jy .............................................. | 315/121 |
| 5,230,792 | 7/1993 | Sauska et al. ............................. | 210/97 |
| 5,324,423 | 6/1994 | Markham .................................. | 210/87 |
| 5,401,394 | 3/1995 | Markham .................................. | 210/85 |
| 5,503,800 | 4/1996 | Free ........................................... | 422/24 |
| 5,536,395 | 7/1996 | Kuennen et al. .......................... | 210/87 |
| 5,547,590 | 8/1996 | Szabo ....................................... | 210/748 |
| 5,611,918 | 3/1997 | Markham .................................. | 210/87 |
| 5,698,091 | 12/1997 | Kuennen et al. .......................... | 210/87 |
| 5,707,594 | 1/1998 | Austin ..................................... | 422/186.3 |
| 5,866,984 | 2/1999 | Doughty et al. ......................... | 313/643 |

*Primary Examiner*—Don Wong
*Assistant Examiner*—Tuyet T. Vo
*Attorney, Agent, or Firm*—Jim Zegeer

[57] ABSTRACT

A low-voltage ballast-free energy-efficient ultra-violet material treatment and purification system and method having an ultraviolet (UV) source comprising a gas discharge UV lamp having spaced electrodes, a source of a low-voltage, high-frequency alternating current square wave voltage and connected directly to the spaced electrodes to non-thermionically excite the gas discharge UV lamp. A flow sensor is used to proportionately control the intensity of UV generation as a function of flow rate.

18 Claims, 2 Drawing Sheets

LOW-VOLTAGE BALLAST-FREE ENERGY-EFFICIENT ULTRAVIOLET MATERIAL TREATMENT AND PURIFICATION SYSTEM AND METHOD

REFERENCE TO RELATED APPLICATIONS

This application is related to U.S. application Ser. No. 08/942,670 filed Oct. 2, 1997 entitled LOW-VOLTAGE NON-THERMIONIC BALLAST-FREE FLUORESCENT LIGHT SYSTEM AND METHOD which in turn was the subject of provisional application Ser. No. 60/053,796 filed Jul. 25, 1997 which are incorporated hereby reference. This application is also a continuation-in-part of my application Ser. No. 08/964,824 for LOW VOLTAGE NON-THERMIONIC BALLAST-FREE ENERGY-EFFICIENT LIGHT-PRODUCING GAS DISCHARGE SYSTEM AND METHOD filed Nov. 5, 1997, now U.S. Pat. No. 6,034,485, and incorporated herein by reference.

Reference is also made to my application Ser. No. 08/915,696 filed Aug. 21, 1997 entitled LOW-VOLTAGE HIGH-EFFICIENCY FLUORESCENT SIGNAGE, PARTICULARLY EXIT SIGN, and now U.S. Pat. No. 5,998,941 and incorporated herein by reference.

BACKGROUND AND BRIEF DESCRIPTION OF THE INVENTION

In a typical fluid treatment purification system utilizing ultraviolet (UV) energy, the fluid, which may be a liquid and/or gaseous substance contaminated by pathogenic organisms is moved through a treatment zone. Typically, the UV energy is provided by causing a discharge in a gaseous medium contained in a UV transmission bulb or envelope. Typical gas fillings include mixtures of argon (and/or other gases such as xenon XE, krypton KR) and mercury which, upon discharge therein, is rich in ultraviolet (other UV rich gases on ionization may be used). Typically, a ballast power supply is connected to the electrodes. In electronic ballast systems, a step-up transformer provides a high striking or ionization voltage, several hundred volts (which, once the lamps are energized, is lowered to a normal operating voltage (normally in the range of 100–200 volts)). When the ultraviolet lamps are used for large scale water purification systems, the lamps, typically a cylindrical ultraviolet ray-emitting lamp and an outer coaxial and substantially coextensive cylindrical UV transparent sleeve, are arranged in banks or arrays in parallel rows. Various structural arrangements are utilized to enable and facilitate the mounting of the banks or arrays of UV lamps in a water-flow conduit for treatment of the water. Typically, the axis of the UV lamps are parallel to the flow direction of the water.

In some systems, the UV source is driven in two or more intensity modes, a low intensity mode when the fluid flow is low and a high intensity mode when the fluid flow is high. Reference is made to the following prior U.S. patents:

| Patent No. | Issued | Inventors |
|---|---|---|
| 4,482,809 | 11/1984 | Maarschalkerweerd |
| 4,872,980 | 10/1989 | Maarschalkerweerd |
| 5,023,518 | 06/1991 | Mans et al |
| 5,081,399 | 01/1992 | Jy |
| 5,230,792 | 07/1993 | Sauska et al |
| 5,324,423 | 06/1994 | Markham |
| 5,401,395 | 03/1995 | Markham |

| Patent No. | Issued | Inventors |
|---|---|---|
| 5,503,800 | 04/1996 | Free |
| 5,536,395 | 07/1996 | Kuennen et al |
| 5,547,590 | 08/1996 | Szabo |
| 5,611,918 | 03/1997 | Markham |
| 5,698,091 | 12/1997 | Kuennen et al |
| 5,707,594 | 01/1998 | Austin |

Sauska et al U.S. Pat. No. 5,230,792 and Markham U.S. Pat. No. 5,611,918 are typical examples of ultraviolet water purification systems with variable intensity controls. In these patents, the intensity of an ultraviolet lamp is controlled by a circuit which is responsive to fluid flow for selectively energizing the lamp to provide variable UV intensity output depending upon fluid flow. In these circuits, a high striking voltage is required to initiate the discharge and produce ultraviolet. In the case of Sauska et al, the circuit arrangement is such that the ultraviolet lamp is always started with a high-current ballast. This is in order to assure the striking of a discharge, and then a low-mode ballast-is used to maintain the UV lamp in the low output stage status.

THE PRESENT INVENTION

The object of the present invention is to provide an improved ultraviolet energy source and, more particularly to provide a low-voltage ballast-free energy-efficient ultraviolet energy source, and still more particularly to provide such a UV source in a fluid treatment system and yet more particularly to provide a significantly more efficient low-voltage, low-current, ultraviolet light-producing system for treatment of various flowing fluids and substances and materials which is useful in killing and/or controlling pathogens, microorganisms, bacterial and other deleterious materials in flowing fluid systems such as water purification and air purification systems.

The UV energy produced by the invention can be used for curing, UV medical treatments, photolithographic applications, enhancing chemical reactions, etc.

Since the ultraviolet energy source of the present invention is significantly lower in power consumption and produces significantly more useful ultraviolet energy/per watt than conventional ultraviolet energy lamps and bulbs that it replaces, fewer lamp units for a given treatment may be required. In addition, since the intensity level can be varied from zero to high intensity and back to zero in an infinitely variable manner, the intensity rate of the ultraviolet energy can be varied in a likewise infinitely variable manner (e.g. step-less variations).

Since heated filaments are not utilized, the device is essentially non-thermionic.

According to the invention, one or more ultraviolet lamps are driven from a low-voltage (4–16 volt range) alternating current square wave power supply driver circuit. The square wave power supply driver circuit incorporates a solid state switch circuit which is operated to generate a substantially square wave alternating wave at the ultraviolet lamp or tube electrode, such that the voltage supply to the electrode reverses polarity more rapidly than the pattern of electron and ion density in the tube can shift so that electrons throughout the length of the space between the electrodes are continually accelerated and will, through several cycles of the applied square wave, create tree electrons and ions throughout the tube volume and ionize the gas-producing ultraviolet energy in a discharge. In the preferred embodiment, the oscillating frequency is set in the range from about 100 kHz to about 1.5 MHz and, more precisely, between 1 MHz and 1.5 MHz. Since there are no high voltages in the driver circuit, safer operation is assured. Variation in intensity levels can be achieved by varying the voltage or energy level from the direct current supply to the driver circuit. In a preferred embodiment, care is taken to assure that there are no spike voltages due to inductive kicks and the like. Since the ultraviolet lamps or devices are non-thermionically driven, e.g. the filaments are not heated, the efficiency of UV production is significantly improved. Moreover, at the high-frequency range, the power supply can be much smaller.

Another feature of the present invention is that in comparison to traditional ultraviolet lamp purification systems there is marked reduction in current, power consumption and heat, accompanied by significant increase in ultraviolet light energy output which in turn is the reason why efficient conversion of electricity to ultraviolet energy is high. Some of the heat (power) reduction is, of course, recognizable as resulting from the absence of direct heating of the filaments in each end of the tube by applied voltages. Some is also explained in terms of energy transfer in the high-field region which occurs near the momentary cathode. However, ultraviolet lamps in the system of the present invention are much cooler throughout their length including areas that are the greatest distances from the filaments or electrodes whose heating could not possibly be explained by conduction, radiation or diffusion heat transferred through the low pressure gas filling the tube. The overall voltage (4–16 volts (preferably in the 6–8 volts range), square wave AC at 100 kHz to about 1.5 MHz with the preferred range being about 1.0 MHz to about 1.5 MHz depending in part on the atomic particles (of a given gas discharge medium)) is not large enough to suggest that local regions of high fields exist in UV tubes driven according to the present invention.

Cooling along the length of the tube is believed to be explainable in terms of energy transferred to electrons and ions by the applied electric field. In the present invention, the square wave applied voltage to the tube reverses so frequently that positive ions in the discharge can build up little kinetic energy during a half-cycle of the applied voltage. In conventional ultraviolet lighting systems driven by discharge (e.g. non-microwave or magnetron driven UV system), larger amounts of energy can be acquired by ions in one-half cycle. This kinetic energy contributes nothing to ultraviolet light production, but in conventional systems is rapidly transferred to neutral gas molecules and thence to the walls of the tube.

A major source of energy loss in conventional ultraviolet tubes is caused by the need to almost completely reconstitute ionization in the tube at the beginning of each half-cycle. This requires not only energy to ionize electrically neutral gas molecules, but additional energy representing losses when electrons collide with neutral gas molecules and thereby increase their motional energy without ionizing the molecules. The fact that the system is non-thermionic and ballast-free eliminates the danger and cause of electrical fires caused by overheated ballast-driven systems. The low voltage eliminates the danger of electrical shock to humans, and because it is low voltage is essentially non-lethal to humans and thus safer to use in water-based applications.

DESCRIPTION OF THE DRAWINGS

The above and other objects, advantages and features of the invention will become more apparent when considered with the following specification and accompanying drawings wherein.

DETAILED DESCRIPTION OF THE INVENTION

Figure 1:
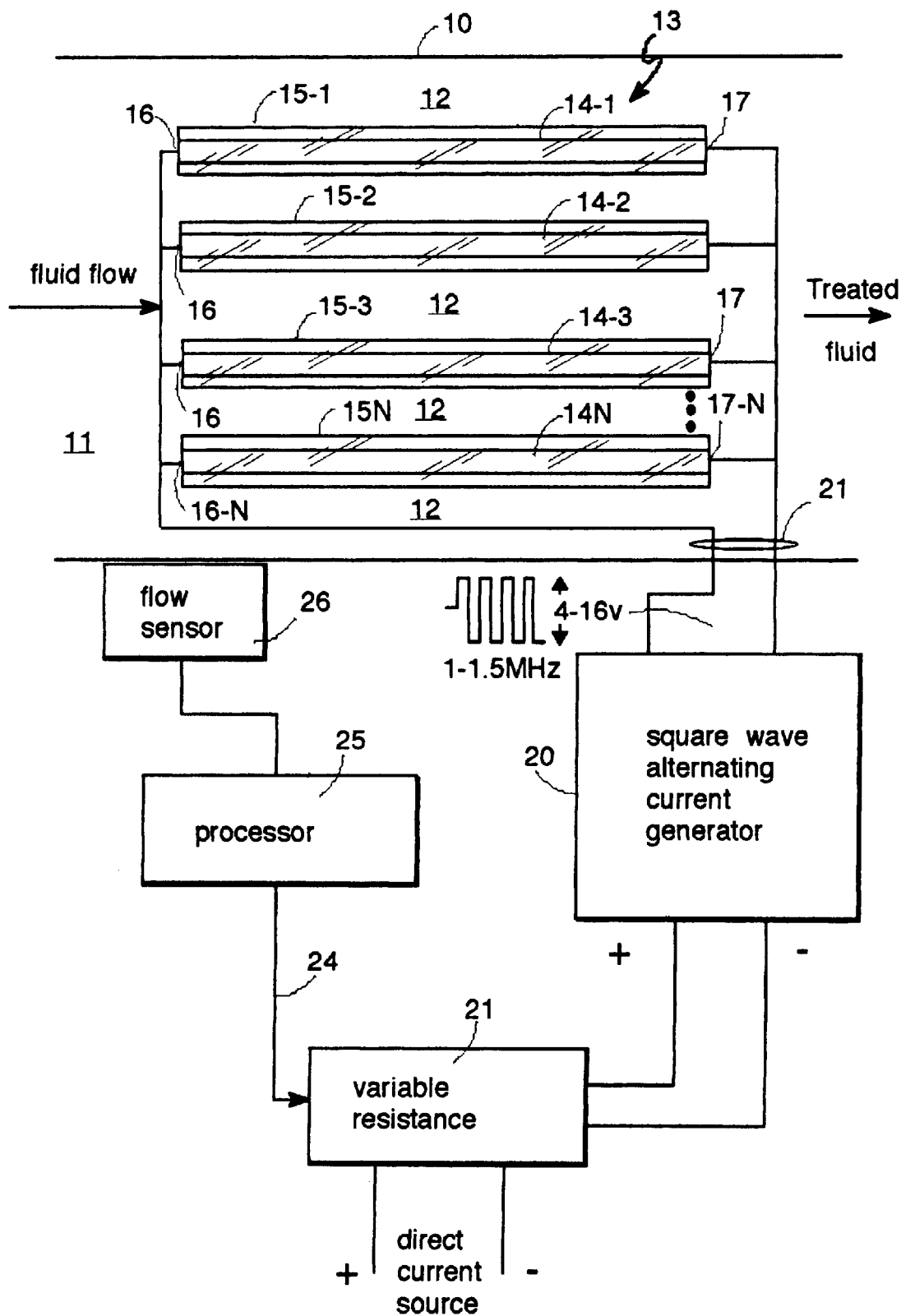
FIG. 1 is a general block diagram of a fluid flow ultraviolet purification and treating system incorporating the invention.

The present invention is based on the discovery, disclosed in my above identified applications, that using a rapidly repetitive low-voltage square wave alternating voltage, ionization will take place in gas discharge devices in the absence of a "striking" voltage at significantly lower voltages and power. Since the half-cycle period of the square wave alternating voltage power according to the invention is very short (of the order of 0.5 microseconds for 1 MHz or 5 microseconds for 100 kHz), there is very little opportunity for decay of the plasma between half-cycles. At start-up, ambient free electrons in the gas increase in energy in a half-cycle more than they lose energy due to collision processes. According to the invention, during one half-cycle, an electron will move in a roughly constant electric field. During each interval between collisions with neutral atoms, or ions, its kinetic energy will increase if its previous collision left it traveling with a component of velocity in the direction of the acceleration produced by the electric field. It will decrease if its previous collision left it moving without a component of velocity opposed to the field's acceleration. According to the invention, the square wave alternating supply voltage serves principally to raise the effective electron energy (or temperature). The current flowing consists of electrons flowing to the instantaneous anode and positive ions flowing to the instantaneous cathode where they recombine with electrons and are released as neutral atoms. Total gas pressure in the tube is sufficient to make the mean free path considerably less than the tube diameter and much less than its length. Most electrons and ions separate and recombine, in a small fraction of the overall length of the tube, rather than flowing as continuous streams along its axis.

If the UV lamp system of the present invention starts at low voltage levels far below that usually associated with plasma "breakdown", why does an equally low voltage applied constantly across a single tube not result in the same glowing plasma? This can be explained in terms of the natural tendency of particles of a plasma subject to a static external electric field to move so as to create a space charge pattern and field that counteracts the applied field. The result of applying a voltage between two electrodes is to induce positive charge on the positive electrode and negative charge on the negative electrode, the absolute amount of charge depending of course on the capacitance between the two.

If free electrons and ions fill the space between these electrodes, the electrons are pulled toward the anode, and the positive ions toward the cathode, until in the space between there is no longer a field and therefore no means to cause further movement of the particles; a voltage drop, that is, region of high field, will exist very close to each of the two electrodes. The electrons (and ions) in the main part of the tube will not be further affected by the field; when electrons reach the high field region near the anode, they will probably be accelerated to half the applied voltage within less than one mean free path of the anode's surface and hence will be unlikely to produce ionization.

Figure 2:
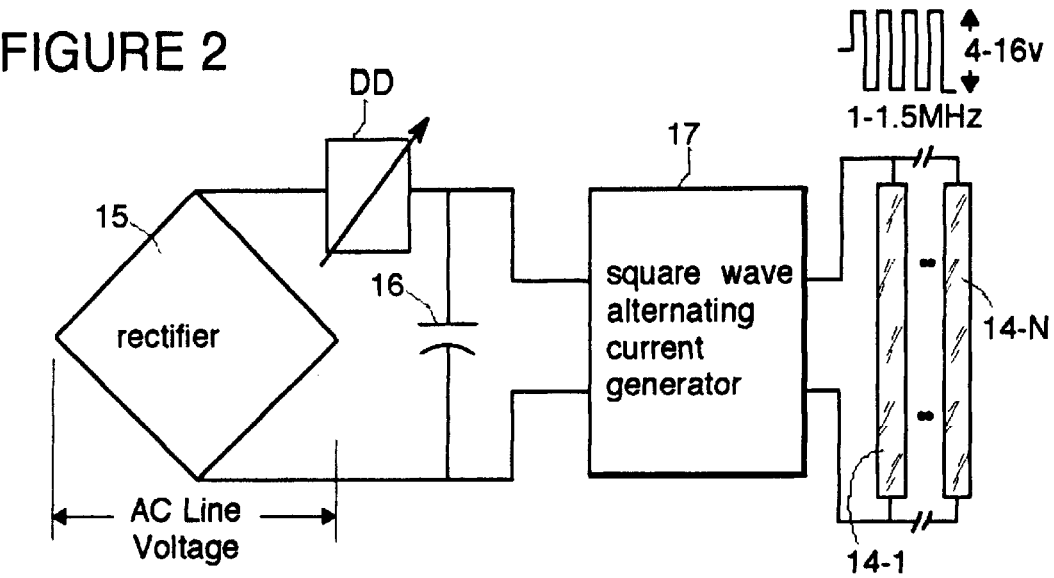
FIG. 2 is a general block diagram of a square wave alternating current generator incorporating the invention.

Referring now to FIG. 1, a tube or conduit 10 contains a flowing fluid 11 which, in this present case, is water. A treatment zone 12 is provided with an array 13 of ultraviolet lamps or tubes 14-1, 14-2 . . . 14-N which are contained within usually transparent quartz tubes 15-1, 15-2. UV tubes or bulbs 14-1, 14-2 . . . 14-N are filled with a conventional gas discharge mixture which is rich in UV production upon discharge, such as 90% argon, 10% neon and 3%–5% of mercury at a pressure of about 10 millibars or Thors. Instead of heated filaments, each tube contains electrodes 16, 17, of the type usually found in neon signage. Of course conventional UV tubes, with the unheated filaments serving as non-thermionic electrodes, can be used. The electrodes 16, 17 are connected by a substantially LC-free circuit to a low-voltage square wave alternating current generator 20 by lead wires 21. Since the voltage is quite low, lead wires 21 need not be expensive or heavily insulated. Square wave alternating current generator 20 is supplied with direct current from a direct current source which may be a bridge rectifier 15 (FIG. 2) connected to an alternating current supply. In a preferred embodiment of the present invention, a variable resistance 21 is interposed between the direct current voltage supply and the low-voltage square wave alternating generator 20 so that the intensity level of ultraviolet energy can be varied by varying the direct current supply to the square wave alternating current generator. The adjustment of the intensity level of ultraviolet light production from low (or zero)-to-high and high-to-low is thus simply and easily achieved.

Referring to FIG. 1, in still a further preferred embodiment of the invention, a flow sensor 26 detects the rate of flow of fluid in conduit or passage 10 and the rate of flow signal output of flow sensor 26 is fed to processor 25 which outputs an intensity control signal 24 which is used to control variable resistance 21. Thus, on no flow of fluid 11 in passage or conduit 10, the flow sensor output is zero so that the processing control signal output is zero so that the variable resistance 21 is essentially high or an open circuit. As fluid flow begins, the flow sensor signal increases and the processor 25 output control signal 24 causes variable resistance 21 to decrease thereby supplying more energy to square wave alternating current generator 20, thereby increasing the energy supplied on lines 21 to the electrodes of UV lamps 14-1, 14-2 . . . 14-N. Thus, as the rate of waterflow reaches the maximum, the maximum energy is supplied to the UV tubes thereby increasing the amount of the ultraviolet energy used to treat the fluent material flowing in conduit 10 to a maximum. Since the controls are variable from zero to a maximum, the maximum ultraviolet energy coincides with the maximum fluid flow rate and the minimum or zero ultraviolet energy coincides with the zero flow rate, and any place in-between the ultraviolet energy generated is directly proportional to the fluid flow rate.

Moreover, the current rate is very low, so, in comparison with ultraviolet output of conventional ultraviolet purification lamps driven by conventional 60 cycle thermionically (heated filaments) operated fluorescent tubes or lamps, the luminous efficiency is significantly improved. Moreover, the ultraviolet lamps or tubes can be straight, folded, helical, looped, etc.

Rheostat or variable resistance 21R is used to adjust or vary the voltage or energy level from the direct current source to the ultraviolet lamp device and thereby dim or vary the intensity of ultraviolet rays produced by the lamps. It will be appreciated that while the UV lamps are shown driven from a single square wave alternating current generator a plurality of square wave alternating current generators can be provided, one for each lamp and each individually controlled according to individual flow conditions adjacent a given lamp or sector. In other words, there can be a plurality of flow sensors, one for each UV lamp or cluster or array of UV lamps controlling the UV production in their energy levels at each lamp in infinitesimally small increments of adjustment. Thus, since the system does not depend on a large or striking ignition voltage level, the energy level from the ultraviolet lamp can be varied from very low to high and back to low. In contrast, the prior art requires a high striking voltage to initiate a discharge in the ultraviolet lamps and cannot start out at low levels as is the case of the present invention.

Figure 3:
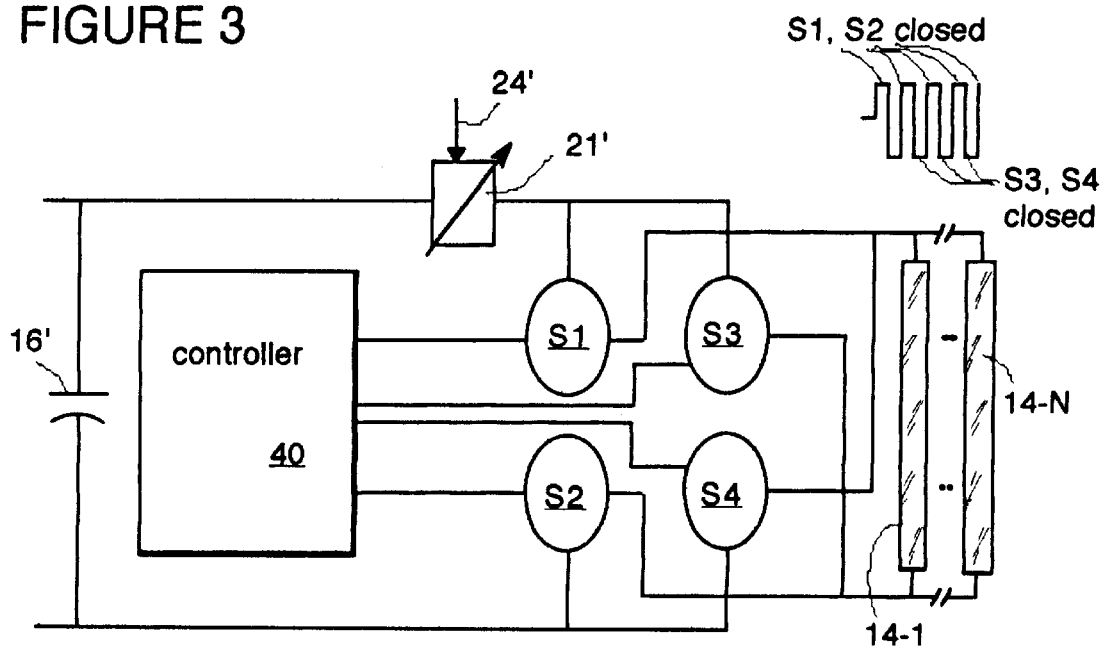
FIG. 3 is a generalized circuit diagram of a square wave alternating current generator incorporating the invention.

In FIG. 3, a transformerless square wave invertor circuit is illustrated wherein the positive (+) and negative (−) terminals of a direct current source are alternately connected to opposing electrodes of the ultraviolet lamp(s). In this case, when switches S1 and S2 are closed simultaneously or at the same time, preferably by the same signal from controller 40, the positive terminal (+) is connected to electrode E-1 and the negative terminal (−) is connected directly to electrode E-2. When the switches S3 and S4 are simultaneously closed (and switches S1 and S2 are open) by controller 40, the positive terminal (+) is connected directly to lamp electrode E-2 and the negative terminal (−) is connected to the electrode E-1 of the ultraviolet lamp. Controller 40 can operate the switches in the range of about 100 kHz to about 1.5 MHz and preferably operates the switches to cause the square wave voltage applied a substantially LC-free circuit to lamp electrodes E-1 and E-2 to be at a frequency of about 1 MHz to about 1.5 MHz.

In this invention, the magnitude of the alternating voltage at the electrodes is of small significance in initiating the discharge reaction, allowing the capability to start the production of ultraviolet light at a low or high intensity—since the generated ultraviolet is in direct proportion to the total energy input. In a preferred embodiment the voltage is in the range of about 4 volts to about 16 volts.

While preferred embodiments of the invention have been described and illustrated, it will be appreciated that other embodiments, adaptations and modifications of the invention will be readily apparent to those skilled in the art.

What is claimed is:

1. In a fluid purification system in which fluid flowing in a path is subjected to ultraviolet (UV) energy, the improvement comprising:

a fluid flow rate sensor for measuring the fluid flow rate of fluid flowing in said path and producing a fluid flow rate control signal, an ultraviolet (UV) source positioned in said path, said UV source having a UV lamp and a square wave alternating current driver circuit connected to said UV lamp to non-thermionically start and operate said lamp with a square wave alternating current voltage, a controller connected to said ultraviolet source and said flow rate sensor for proportionately controlling the intensity of ultraviolet energy emitted in said path by said intensity control as a function of said fluid flow rate control signal.

2. In an ultraviolet (UV) material treatment system, the improvement comprising an ultraviolet (UV) source, said UV source comprising in combination:

a UV lamp and a source of low-voltage, high-frequency, square wave alternating voltage in the frequency range of about 100 kHz to about 1.5 MHz connected to said UV lamp to non-thermionically start and operate said UV lamp.

3. The ultraviolet material treatment system defined in claim 2 including a device to proportionally vary the UV intensity level from said UV lamp as a function of the quantity of material treated thereby.

4. A method of non-thermionically energizing an ultraviolet (UV) lamp device having spaced electrodes immersed in a gas at voltages far below the required starter ignition voltage for cold cathodes comprising:

providing a low-voltage square wave alternating voltage source of between about 4–16 volts and between about 100 kHz and 1.5 MHz, and applying said low-voltage square wave alternating voltage from said source directly to said UV device so that the voltage on said UV lamp electrodes reverses its polarity more rapidly than the pattern of electron and ion density in the gas can shift.

5. The method defined in claim 4 including varying the energy level from said source to said UV lamp to vary the UV energy level emitted thereby.

6. An ultraviolet (UV) source comprising one or more UV lamps, each UV lamp having a transparent envelope filled with a gas emitting UV on ionization thereof, spaced electrodes in each of said one or more envelopes, respectively, and a source of low voltage, high-frequency square wave alternating voltage directly connected to said electrodes to non-thermionically start and operate said UV lamp.

7. The UV source defined in claim 6 wherein said source of low voltage, high-frequency square-wave alternating voltage is variable.

8. The UV source defined in claim 9 wherein said source of low voltage, high-frequency square-wave alternating voltage is variable.

9. A fluid purification system comprising a fluid flow path, a treatment zone in said fluid flow path and one or more of the UV sources defined in claim 6 in said treatment zone.

10. The invention defined in claim 9 including a flow rate sensor for measuring fluid flow rate in said treatment zone and producing a control signal for said variable source to proportionately vary the UV intensity level of said UV source.

11. A non-thermionic ultraviolet (UV) source comprising in combination a gas discharge UV lamp having spaced electrodes, a source of a low-voltage, high-frequency alternating current square wave voltage and a circuit applying said low-voltage, high frequency square wave voltage to said spaced electrodes of said gas UV discharge lamp wherein said spaced electrodes are non-thermionically excited.

12. The UV source defined in claim 11 wherein said low voltage is in the range of about 4 volts to about 16 volts.

13. The UV source defined in claim 11 wherein said low voltage is in the range of about 4 to about 16 volts and has a frequency in the range of about 100 kHz to about 1.5 MHz.

14. The UV source defined in claim 11 wherein said voltage is about 8–16 volts.

15. The UV source defined in claim 11 wherein said low-voltage, high-frequency square wave voltage is in the frequency range of about 100 kHz to about 1.5 MHz.

16. The UV source defined in claim 15 wherein said low-voltage, high-frequency square wave voltage has a frequency of about 1 MHz.

17. The non-thermionic UV source defined in claim 11 including a controller for controlling the energy level of said source of square wave alternating current voltage supplied to said UV lamp.

18. The non-thermionic UV source defined in claim 17 wherein said controller includes a rheostat.

* * * * *